United States Patent [19]

Ito

[11] 4,430,216

[45] Feb. 7, 1984

[54] HIGH SPEED PREPARATIVE COUNTERCURRENT CHROMATOGRAPHY WITH A MULTIPLE LAYER COILED COLUMN

[75] Inventor: Yoichiro Ito, Bethesda, Md.

[73] Assignee: The United States of America as represented by the Department of Health and Human Services, Washington, D.C.

[21] Appl. No.: 416,107

[22] Filed: Sep. 9, 1982

[51] Int. Cl.$^3$ .............................................. B01N 15/08
[52] U.S. Cl. .................................... 210/198.2; 210/511
[58] Field of Search ...................... 210/657, 198.2, 781, 210/287, 511, 635

[56] References Cited

U.S. PATENT DOCUMENTS

| 3,856,669 | 12/1974 | Ito et al. | 210/657 X |
| 4,058,460 | 11/1977 | Ito | 210/198.2 |
| 4,287,061 | 9/1981 | Sutherland | 210/198.2 |

Primary Examiner—John Adee
Attorney, Agent, or Firm—Browdy and Neimark

[57] ABSTRACT

A horizontal flow-through apparatus for two-phase countercurrent chromatography consisting of a horizontal multi-layer helically coiled column carried on a flanged reel which is rotated about its own axis and simultaneously revolved around a stationary central parallel horizontal pipe at the same angular velocity and in the same direction to prevent twisting of its inlet and outlet flow tubes, which extend through the stationary central pipe. The multi-layer array can retain a large volume of the stationary phase against a high flow rate of the mobile phase, enabling the separation of the sample components to be completed in a relatively short period of time.

13 Claims, 3 Drawing Figures

HIGH SPEED PREPARATIVE COUNTERCURRENT CHROMATOGRAPHY WITH A MULTIPLE LAYER COILED COLUMN

FIELD OF THE INVENTION

This invention relates to continuous countercurrent chromatography systems, and more particularly to a system for continuous countercurrent chromatography which employs a horizontal multi-layer coiled helical tubular array rotating on its longitudinal axis.

BACKGROUND OF THE INVENTION

Performance of preparative CCC (countercurrent chromatography) systems mainly depends upon the amount of the stationary phase retained in the column, which determines both the resolving power of the solute peaks and the sample loading capacity. Various CCC systems developed in the past (see Y. Ito, J. Biochem, Biophys. Met., 5 (1981) 105) are usually capable of yielding retention of the stationary phase of no more than 50% of the total column space. This maximum attainable retention level tends to fall rather sharply with the application of higher flow rates of the mobile phase, resulting in loss of peak resolution. Consequently, the applicable flow rate has become one of the major limiting factors in CCC, and the methods require relatively long separation times ranging from overnight to several days to complete a sizable separation. There is a definite need for an improved CCC system which can perform using a high feed rate of the sample solution and which requires a substantially shorter separation time (see Y. Ito, J. Chromatogr., 207 (1981) 161).

SUMMARY OF THE INVENTION

As a result of efforts made to develop a new CCC system which performs efficient extraction under a high feed rate of the sample solution, it has been found that the use of a multiple-layer coiled column (a coiled tube wound on a reel) becomes ideal for performing preparative CCC, for example, as demonstrated on a preliminary separation of DNP amino acids with a conventional two-phase solvent system (see Y. Ito, J. Chromatogr., 214 (1981) 122). Because of a high flow rate of the mobile phase, together with excellent retention of the stationary phase, this system can provide efficient chromatographic separation on a preparative scale within several hours.

The system of the present invention utilizes a previously known complex hydrodynamic motion of two immiscible solvent phases in a rotating coiled tube. Let us consider a simple model which consists of a coil coaxially mounted around a rotary shaft held in the horizontal position. When the coil is filled with water and is slowly rotated around its own axis, any object, either heavier (such as a glass bead) or lighter, (such as an air bubble) than the water present in the coil tends to move toward one end of the coil. This end is then called the "head" and the other end, the "tail" of the coil. When the coil is filled with two immiscible solvent phases, rotation sooner or later establishes a hydrodynamic equilibrium between the two solvent phases, where the two phases are distributed in each helical turn at a given volume ratio (equilibrium volume ratio) and any excess of either phase remains at the tail of the coil.

This hydrodynamic equilibrium can be efficiently utilized for performing CCC. When the coil is eluted with one of the phases through the head end, the hydrodynamic equilibrium tends to maintain the original equilibrium volume ratio of the two phases in the coil and thereby a certain volume of the other phase is permanently retained in the coil while the two phases are undergoing vigorous agitation with rotation of the coil. Consequently, the sample solutes introduced locally at the inlet of the coil are subjected to an efficient partition process between the two phases and are chromatographically separated according to their partition coefficients in the absence of solid supports.

In this CCC scheme, the volume of the stationary phase retained in the coil is mainly determined by the following two factors: One is the equilibrium volume ratio of the two phases before the elution is started, and this determines the maximum attainable retention level of the stationary phase. When the mobile phase is introduced into the coil, it displaces a part of the stationary phase to alter the equilibrium volume ratio, where the rate of movement of the mobile phase toward the tail is just balanced by the rate of movement of the stationary phase returning toward the head. This returning rate of the stationary phase is the other important factor which determines the actual retention level of the stationary phase at a given flow rate of the mobile phase. The higher the relative rate of the stationary phase against that of the flowing mobile phase, the greater is the volume of the stationary phase retained in the coil, but always within the maximum attainable level determined by the initial equilibrium volume ratio of the two phases. In order to achieve a satisfactory retention level of the stationary phase against a high flow rate of the mobile phase, the CCC scheme should produce not only a large initial equilibrium volume ratio of the stationary to the mobile phases, but also a high flow rate of the stationary phase toward the head of the coil against the flowing mobile phase. Although the simple rotary coil device described above may give a desired equilibrium volume ratio to the stationary phase at the optimum rotational speed of the coil, the scheme fails to produce a sufficiently high flow rate of the stationary phase under the unit gravitational field.

Accordingly, a main object of the present invention is to provide an improved CCC system which overcomes the deficiencies and disadvantages of the previously employed horizontal CCC systems.

A further object of the invention is to provide an improved CCC system yielding a relatively high flow rate of the stationary phase under the unit gravitational field.

A still further object of the invention is to provide an improved horizontal CCC flow-through system using a multi-layer coiled column which can retain a large volume of the stationary phase against a high flow rate of the mobile phase, enabling separation to be completed within a few hours, as compared with much longer times required for such separation using previously known column constructions.

A still further object of the invention is to provide an improved flow-through coil planet centrifuge which provides an efficient chromatographic separation of solutes on a preparative scale within 2 to 5 hours, by the use of a multiple-layer coiled column, which promotes retention of the stationary phase under a high flow rate of the mobile phase and permits application of the device to conventional two phase systems, and which can be employed successfully for a wide range of various biological samples, such as DNP amino acids, oligopeptides, gramicidins, auxins, and purines and pyrimidines.

BRIEF DESCRIPTION OF THE DRAWINGS

Further objects and advantages of the invention will become apparent from the following description and claims, and from the accompanying drawings, wherein:

DETAILED DESCRIPTION OF A PREFERRED EMBODIMENT

Figure 1:
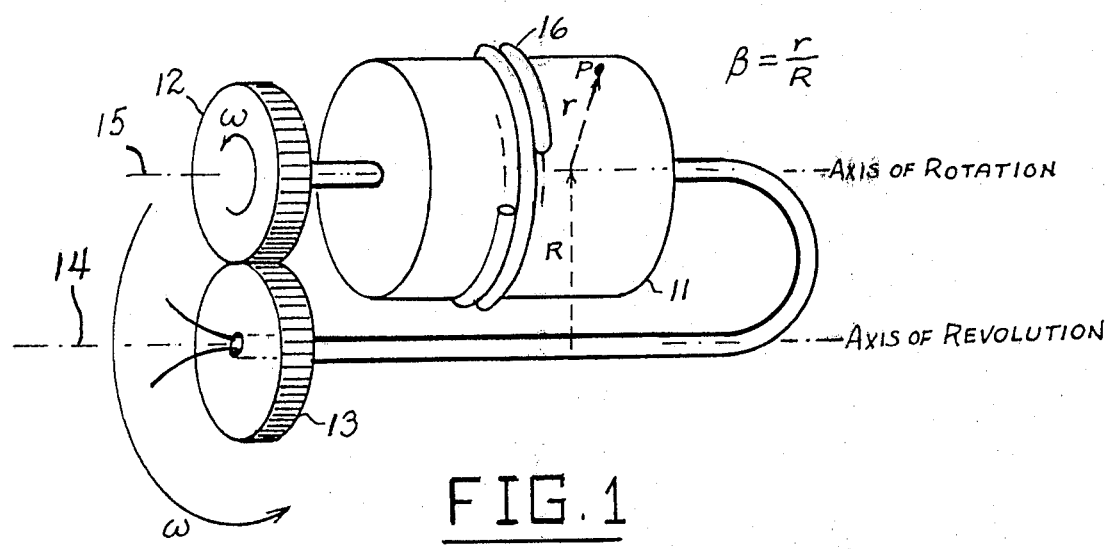
FIG. 1 is a diagram illustrating a coil subjected to a type of synchronous planetary motion similar to that employed in the present invention.
Figure 3:
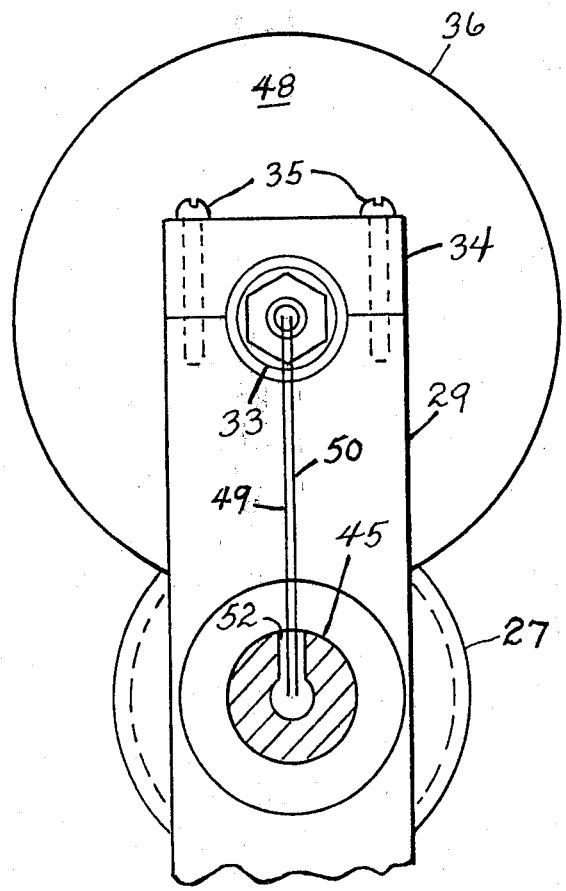
FIG. 3 is a fragmentary transverse vertical cross-sectional view taken substantially on line 3—3 of FIG. 2.

Recently it has been found that the above-mentioned basic requirements are satisfied by subjecting a coil to a particular type of synchronous planetary motion produced by a centrifuge arrangement schematically illustrated in FIG. 1. A large cylindrical coil holder 11 coaxially is provided with a planetary gear 12 which is gearingly coupled to an identical stationary sun gear 13 mounted on the central axis 14 of the centrifuge. This gear arrangement produces a synchronous planetary motion of the coil holder 11. The holder 11 revolves around the central axis 14 of the apparatus and simultaneously rotates about its own axis 15 at the same angular velocity $\omega$ in the same direction. In so doing the holder 11 always maintains its axis 15 parallel to and at distance R from the central axis 14 of the apparatus. The single-layer coil is prepared by winding a piece of flexible tubing 16 around the holder 11 having a radius r, as shown in FIG. 1.

The centrifugal force field produced by this type of planetary motion has been previously analyzed (see Y. Ito, J. Chromatogr., 188 (1980) 33, and J. Chromatogr. 192 (1980) 75). The results show that the centrifugal force field greatly varies with the location of point P on the holder 11, which is conveniently expressed as $\beta = r/R$, i.e., the ratio between the radii of rotation and revolution. When $\beta$ is greater than 0.25, the centrifugal force vector is always directed outwardly from the inside of the holder while it periodically fluctuates in both magnitude and direction during each revolutional cycle.

A series of preliminary experiments has been performed to study the effects of such centrifugal force fields on the motion of two immiscible solvents in the coil (see Y. Ito, J. Chromatogr. 207 (1981) 161). Observations made with prototypes on various types of two-phase solvent systems revealed that this type of the centrifugal force field establishes a favorable hydrodynamic equilibrium in the coil in such a way that the upper phase always largely dominates on the head side of the coil. With a given pair of the solvent phases, the application of a higher revolutional speed on a large helical diameter coil increases both the equilibrium volume ratio and the flow rate of each phase through the coil to produce more favorable conditions for the retention of the stationary phase.

Among various physical properties of the solvent system, relative density, viscosity and tube-wall affinity of the two phases seem to play the most remarkable role in retention of the stationary phase. When the upper phase is much lighter, less viscous and of higher wall affinity than the lower phase, the two phases are quickly and completely separated along the length of the coil, the upper phase entirely occupying the head side and the lower phase, the tail side of the coil. Under these circumstances, an excellent retention of the stationary phase is accomplished by introducing either the lower phase through the head of the coil or the upper phase through the tail of the coil, after filling the coil with the other phase as the stationary phase. The solvent pairs which provide this ideal performance include (if PTFE tubing is used as the column) a number of useful extraction media such as hexane, ether, ethylacetate, toluene, methyl ethyl ketone, benzene, etc., mixed with aqueous solution where various salts can be added to adjust the pH and ionic strength of the aqueous phase to obtain suitable partition coefficients of solutes for separation.

When the upper phase has higher viscosity and/or less wall affinity than the lower phase, the system of FIG. 1 usually fails to achieve the complete separation of the two phases along the length of the coil and, instead, produces a hydrodynamic equilibrium of the two phases with the upper phase dominating in volume on the head side of the coil. In this case, the choice of the mobile phase is limited to the lower phase which can be introduced at the head of the coil initially filled with the stationary upper phase. Introduction of the upper phase through the tail of the coil containing the stationary lower phase would result in steady carryover of the stationary phase through the head where a small amount of the lower phase is always present under this dynamic equilibrium condition. Several commonly used solvent systems such as n-butanol, sec.-butabol, chloroform and ethylene dichloride, each mixed with an aqueous solution are included in this group.

Figure 2:
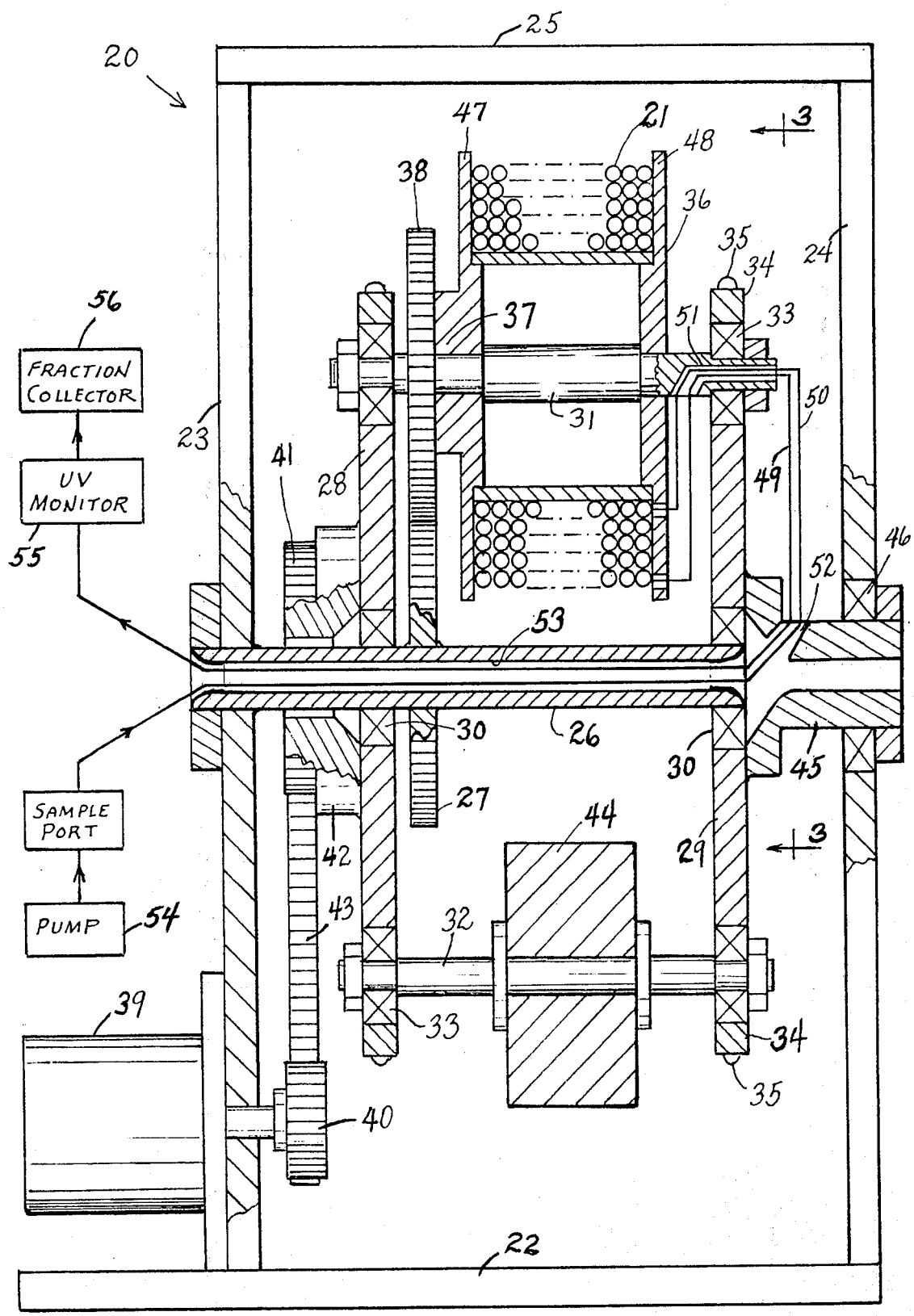
FIG. 2 is a detailed vertical cross-sectional view, partly in elevation, taken through an improved multiple-layer coiled column countercurrent chromatography system constructed in accordance with the present invention.

However, the lack of versatility in the choice of the mobile phase in the above scheme is greatly improved if the column is made by winding a single piece of tubing onto a reel-shaped holder to make multiple layers of the coil column, for example as illustrated in FIG. 2. The holder with the multiple-layer coiled column is rotated always in one direction so that the internal terminal of the column becomes the head and the external terminal becomes the tail. Because of this spiral configuration, a gradient of the centrifugal force field is created along the length of the column from the internal layer of the coil toward the external layer of the coil. This gradient forces the upper phase to move toward the head and the lower phase toward the tail. As a result, the hydrodynamic equilibrium of the solvent systems is altered in a moe favorable way such that the two phases are completely separated along the length of the column, and therefore, either phase becomes usable as the mobile phase without carryover of the stationary phase.

Referring to FIG. 2, 20 generally designates a typical design of an improved coil planet centrifuge with a multiple-layer column 21 according to the present invention. The assembly 20 is supported on a base plate 22 to which are rigidly secured opposite parallel vertical upstanding wall members 23, 24, rigidly connected by a top plate 25. A horizontal central stationary pipe 26 is rigidly secured to and extends through vertical wall member 23. A sun gear 27 is rigidly secured on pipe 26. A pair of spaced parallel support bars 28, 29 are perpendicularly journalled on stationary pipe 26 by means of bearings 30. Respective horizontal shafts 31 and 32 are journalled between the outer portions of support bars 28, 29 by means of bearings 33, retentively engaged by detachable bearing blocks 34 secured to the ends of the support bars by means of fastening screws 35. Secured on shaft 31 is a flanged reel 36 on which is wound the multi-layer column 21. Rigidly secured to the hub 37 of reel 36 is a planetary gear 38 identical to stationary sun gear 27 and meshingly engaged therewith. A motor 39 is mounted on the lower portion of wall member 23 and has a toothed pulley 40 which is drivingly coupled via a toothed belt 43 to a driven toothed pulley 41 rigidly secured to the central portion of support bar 28 coaxially with pipe 26 via an annular boss 42. A counterweight 44 is mounted on shaft 32 opposite reel 36. For mechanical stability, the midportion of support bar 29 is rigidly connected to a short coupling pipe 45 which is supportingly journalled in wall member 24 by means of a bearing unit 46.

In operation, motor 39 drives the rotor frame defined by elements 28, 29, 31, 32 around the central stationary pipe 26 by means of the toothed pulleys 40, 41 and the toothed belt 43. In a typical design, the coil holder 36 and counterweight 44 are symmetrically located at a distance of 10 cm from the central axis of the centrifuge. The planetary gear 38 and sun gear 27 produce the desired synchronously planetary motion of the holder 36. The holder 36 revolves around the central axis of the apparatus and synchronously rotates about its own axis in the same direction.

Both the coil holder 36 and the counterweight 44 are readily removable by loosening the fastening screws 35, which facilitates the preparation of the coiled column 21. The multiple-layer coiled column 21 is prepared by winding a long piece of PTFE tubing tightly around the coil holder 36 between the retaining flanges of the holder, shown at 47, 48, to form multiple layers of the coil 21 up to the rims of the flanges, the terminals of the column being connected to respective flow tubes 49, 50 of the proper diameter. The pair of tubes are first led through an end bore 51 in shaft 30 and then are passed through a side hole 52 in pipe 45 to enter the bore 53 of the central stationary pipe 26. These flow tubes are lubricated with grease and preferably are futher protected from abrasion damage by employing a surrounding lining of Tygon at each supporting end portion of the bore of stationary pipe 26 to prevent direct contact of the flow tubes with metal parts.

The revolutional speed of the apparatus preferably is continuously regulated up to a speed of 800 rpm by employing a speed control unit (Electro Craft or Bodine Electric Co.) having high accuracy and stability. In a typical embodiment, the apparatus was in the form of a compact table model measuring about 17×17×17 inches. The solvent was pumped by means of a Milton Roy Mini Pump 54, and the effluent was continuously monitored by an LKB Uvicord S, shown at 55, at 280 nm, and fractionated into test tubes by means of an LKB fraction collector, shown at 56, for further analysis.

Twisting of the flow tubes 49, 50 is avoided because of the planetary revolution of the column holder 36 in the same direction as, and at the same angular velocity $\omega$ as its rotation around its own axis.

While a specific embodiment of an improved continuous countercurrent chromatography apparatus has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

For example, while the invention has been described with respect to the apparatus being disposed horizontally and rotated about a horizontal axis, it will be understood that when the apparatus is rotated at a high revolutional speed it can be disposed in any orientation. Thus, while gravity plays an important role when the apparatus is slowly rotated and in such cases the apparatus should be disposed horizontally, at a high revolutional speed the effects of gravity become negligible and the apparatus can be in any orientation with respect to the earth.

What is claimed is:

1. An apparatus for continuous countercurrent chromatography comprising a support, helical separation column means including means to retain a large volume of stationary phase comprising a multi-layer helically coiled column rotatably mounted on the support on a first axis, inlet and outlet flow tubes connected to the terminal ends of said multi-layer coiled column, and means to simultaneously rotate said multi-layer coiled column around said first axis and revolve it around a second axis spaced from and being parallel to said first axis, whereby to simultaneously develop both force reversals and centrifugal forces in said multi-layer coiled column.

2. The apparatus of claim 1, wherein said coiled column is mounted horizontally with said first and second axes being horizontal.

3. The apparatus of claim 2, and fixed elongated tubular guide means extending along said second axis and receiving said flow tubes and defining a protective housing for said flow tubes.

4. The apparatus of claim 3, and means to simultaneously rotate said multi-layer coiled column around said first axis and revolve said multi-layer coiled column around said second axis at relative rates avoiding twisting of said flow tubes.

5. The apparatus of claim 2, and wherein said support includes spaced parallel bar members mounted for rotation around said second axis, means rotatably mounting said multi-layer coiled column on said first axis between end portions of said bar members, and counterweight means connected to opposite end portions of said bar members substantially symmetrically relative to said helically coiled column.

6. The apparatus of claim 5, and wherein said means rotatably mounting said multi-layer coiled column includes detachable bearing retention means rotatably securing said coiled column to the outer ends of said bar members.

7. The apparatus of claim 2, and wherein said support includes a pair of spaced parallel bar members mounted for rotation around said second axis, and wherein said multi-layer coiled column comprises a supporting reel with the multi-layer column helically wound thereon, said reel having an axial shaft journalled between end portions of said parallel bar members.

8. The apparatus of claim 7, and counterweight means connected between the opposite end portions of said spaced parallel bar members substantially symmetrically relative to said supporting reel.

9. The apparatus of claim 7, and fixed elongated tubular guide means extending along said second axis and protectively receiving said flow tubes.

10. The apparatus of claim 7, and fixed elongated tubular guide means extending along said second axis and protectively receiving said flow tubes, and wherein said means to simultaneously rotate said multi-layer coiled column and revove it comprises a fixed sun gear on said tubular guide means and a planet gear on said reel shaft meshing with said fixed sun gear, and drive means to rotate said parallel bar members around said second axis.

11. The apparatus of claim 10, and wherein said planet gear and sun gear are identical, whereby to avoid twisting of said flow tubes.

12. The apparatus of claim 10, and wherein said bar members are journalled on said fixed tubular guide means.

13. The apparatus of claim 12, and counterweight means mounted between the end portions of said bar members substantially symmetrically opposite to said supporting reel.

* * * * *